(12) United States Patent
Ward

(10) Patent No.: US 7,157,528 B2
(45) Date of Patent: Jan. 2, 2007

(54) PERMSELECTIVE STRUCTURALLY ROBUST MEMBRANE MATERIAL

(75) Inventor: Robert S. Ward, Lafayette, CA (US)

(73) Assignee: The Polymer Technology Group, Berkeley, CA (US)

( * ) Notice: Subject to any disclaimer, the term of this patent is extended or adjusted under 35 U.S.C. 154(b) by 0 days.

(21) Appl. No.: 10/851,809

(22) Filed: May 21, 2004

(65) Prior Publication Data

US 2005/0004324 A1 Jan. 6, 2005

Related U.S. Application Data

(60) Provisional application No. 60/473,015, filed on May 21, 2003.

(51) Int. Cl.
*C08G 77/42* (2006.01)
(52) U.S. Cl. ........... 525/474; 525/462; 600/347; 204/403.11
(58) Field of Classification Search ............ 525/474, 525/462; 600/347; 204/403.11
See application file for complete search history.

(56) References Cited

U.S. PATENT DOCUMENTS

| 4,686,044 | A |   | 8/1987  | Behnke et al. ........ 210/500.22 |
| 5,322,063 | A | * | 6/1994  | Allen et al. ............... 600/347 |
| 5,428,123 | A |   | 6/1995  | Ward et al. ................. 528/28 |
| 5,589,563 | A |   | 12/1996 | Ward et al. ................. 528/44 |
| 5,756,632 | A |   | 5/1998  | Ward et al. ................. 528/28 |
| 5,777,060 | A | * | 7/1998  | Van Antwerp ............. 528/28 |
| 5,863,627 | A |   | 1/1999  | Szycher et al. .......... 428/36.8 |
| 5,962,620 | A | * | 10/1999 | Reich et al. ............... 528/76 |
| 6,083,524 | A |   | 7/2000  | Sawhney et al. ......... 424/426 |
| 6,172,180 | B1 |  | 1/2001  | Hancock et al. .......... 528/391 |
| 6,206,835 | B1 |  | 3/2001  | Spillman, Jr. et al. ..... 600/485 |
| 6,313,254 | B1 |  | 11/2001 | Meijs et al. ............... 528/26 |

* cited by examiner

*Primary Examiner*—Kuo-Liang Peng
(74) *Attorney, Agent, or Firm*—Schwabe Williamson & Wyatt

(57) ABSTRACT

A biocompatible multipolymer, having a backbone comprising about 10 to 45 wt % of at least one hard segment and about 55 to 90 wt % of soft segments. The soft segments are divided into three groups, 5 to 25 wt %, of total soft segment weight, of an oxygen permeable soft segment; 5 to 25 wt %, of total soft segment weight, of a hydrophilic soft segment; and 50 to 90 wt %, of total soft segment weight, of a biostable, relatively hydrophobic soft segment.

10 Claims, 1 Drawing Sheet

———  1 polyurethane hard segments

············  2 oxygen permeable soft segments

—·—·—  3 hydrophilic soft segments

— — — —  4 biostable polycarbonate soft segments

PERMSELECTIVE STRUCTURALLY ROBUST MEMBRANE MATERIAL

RELATED APPLICATIONS

The present patent application claims priority from provisional application Ser. No. 60/473,015, filed May 21, 2003, which is incorporated herein by reference as if fully set forth herein.

BACKGROUND OF THE INVENTION

U.S. Pat. Nos. 5,428,123; 5,589,563; and 5,756,632, issued Jun. 27, 1995; Dec. 31, 1996 and May 28, 1998, respectively, together disclose a type of material and a way of engineering this material to have a particular permselectivity. All three of these patents are hereby incorporated by reference as if set forth in their entirety herein. When efforts were made, however, to use this material in an indwelling glucose sensor application it was found that the requirement for high oxygen and glucose permeability was at conflict with the requirement for structural strength and integrity after exposure to an oxidative environment. More specifically it was found that when the material was made sufficiently oxygen permeable it became too weak and tended to break apart on the sensor, after being placed in the body's interstitial fluid for more than a few hours.

Within biological solutions such as blood or interstitial fluid there exist a number of reactive materials and enzymes that may bring about cleavage of the polymer's molecular chains and thus result in loss of membrane or fiber strength and integrity. Some of the reactive materials and enzymes that may bring about polymer degradation and cleavage include small molecules such as superoxide ($O_2^-$) and acids, and enzymes such as proteases and oxidases that react with the various types of linkages in the polymer. This loss of membrane or fiber integrity is deleterious to applications which depend on the permselectivity of the polymeric material and the exclusion of solids and larger biological molecules, such as the detection of the levels of glucose within the body fluids of a living human body.

SUMMARY

In a first separate embodiment, the present invention is a biocompatible hydrophilic segmented block multi polymer, having a backbone comprising about 10 to 45 wt % of at least one hard segment and about 55 to 90 wt % of soft segments. The soft segments are divided into three groups, 5 to 25 wt %, of total soft segment weight, of an oxygen permeable soft segment; 5 to 25 wt %, of total soft segment weight, of a hydrophilic soft segment; and 50 to 90 wt %, of total soft segment weight, of a biostable, hydrophobic soft segment.

In a second separate aspect, the present invention is a biocompatible hydrophilic segmented block multi polymer, being permeable to glucose and wherein its water absorption and hydrophilic soft segment volume are less than 75% of its total dry polymer volume.

The foregoing and other objectives, features and advantages of the invention will be more readily understood upon consideration of the following detailed description of the invention, taken in conjunction with the accompanying drawings.

BRIEF DESCRIPTION OF THE DRAWINGS

Drawing 1 is an illustration of a possible arrangement of the hard segments and soft segments of several polymer chains in a biocompatible multipolymer according to the present invention.

DETAILED DESCRIPTION OF THE PREFERRED EMBODIMENTS

Figure 1:
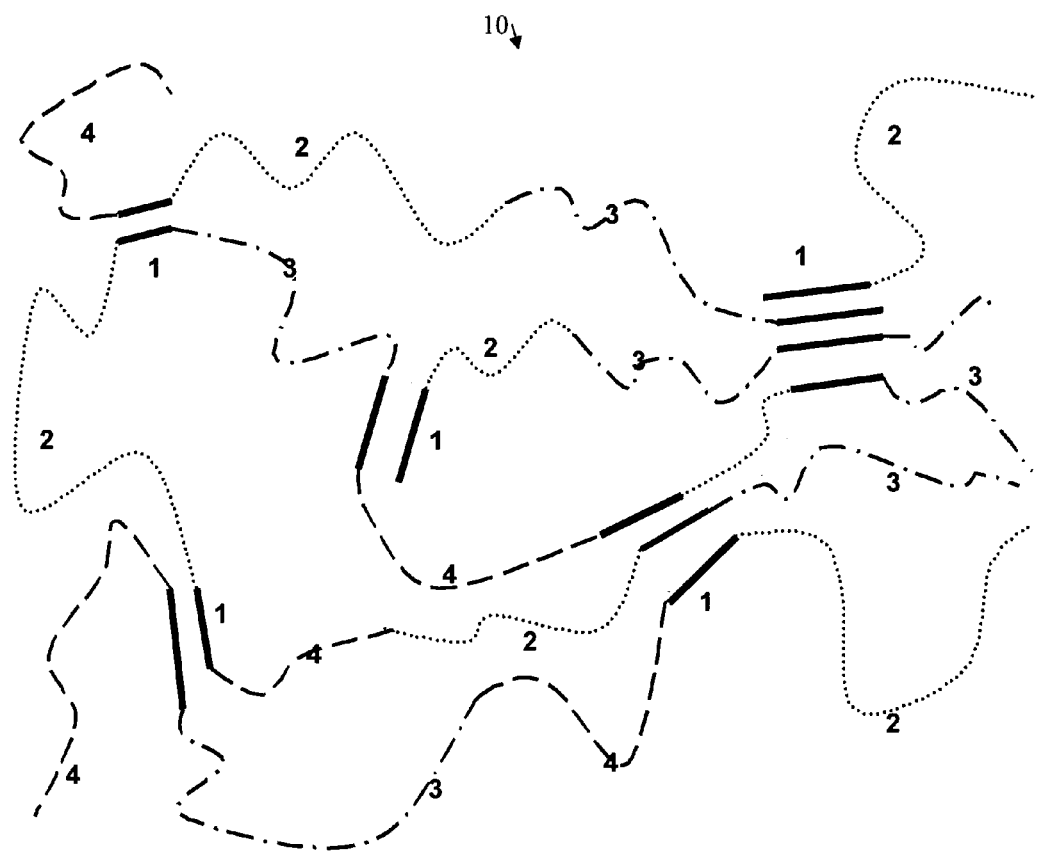

In its preferred embodiments, the present invention is a multipolymer 10, a high molecular weight polymeric organic material consisting of different types of monomeric units, suitable for use in a glucose sensor or in an oxygen sensor which is immersed for substantial periods of time in blood or interstitial fluids of the human body. Referring to FIG. 1 multipolymer 10 includes hard segments 1, polyurethane domains with highly crystalline or glassy nature that associate with each other either interchain to provide the physical tensile strength of membranes made from the polymer. The energetically favorable associations between the individual molecular backbones provide regions that hold the chains together and require a substantial energy input to disrupt. Soft segments of the three different types, oxygen-permeable soft segments 2, hydrophilic soft segments 3, and biostable polycarbonate soft segments 4, are randomly situated in the individual molecular chains. Any type of soft segment may be directly attached to a hard segment, or to another type of soft segment. There may be multiple domains of each kind of segment, hard or soft, in the polymer material. The soft segments have a low associative energy with other soft segments or with hard segments, so a lesser degree of force would be required to dissociate the soft segments, giving membranes prepared from the polymer a rubbery or flexible character. The less crystalline or glassy nature of regions containing soft segments are the regions where oxygen and aqueous solutions may freely permeate the membrane. The polycarbonate soft segments 4 likewise are less crystalline or glassy than the hard segments 1, but their resistance to degradation by the reactive chemicals and enzymes found in the tissue fluids of living human beings gives a greater degree of biostability to membranes prepared from the polymer of the present invention containing such polycarbonate domains.

Again referring to FIG. 1, more specifically, in one preferred embodiment the multipolymer consists of (1) hard segments or domains of substantially crystalline or glassy structure 1, that would have a high melting points or glass transition temperatures if prepared as homopolymers, and (2) soft segments, of substantially amorphous structure 2, 3, and 4, that would have low melting or glass transition temperatures if prepared as homopolymers, that are permeable to aqueous solutions containing organic solutes such as glucose, and to dissolved oxygen, and are substantially stable to degradation in a biological environment. These soft domains (2, 3, 4) are oligomeric or polymeric segments of materials which intersperse and separate the hard domains 1 of the multipolymer, which further comprise three distinct types or classes of polymeric materials: (i) polymer domains 2 that confer oxygen permeability to the material, (ii) polymer domains 3 that confer hydrophilicity to the material, and (iii) polymer domains 4 that confer biostability to the material, specifically domains comprising polycarbonate-type structures.

The hard domains 1 of the multipolymer confer physical strength and durability allowing the casting of dense, non-porous semi-permeable membranes or hollow fibers with sufficient tensile strength and elasticity for use over relatively long periods of times immersed in fluids of the human body. The hard domains of the multipolymer comprise polyurethane structures that may also contain some urea-type linkages (N—(CO)—N) as well as urethane-type linkages (N—(CO)—O). These polyurethane-type polymers result from the reaction of various types of difunctional isocyanates (isocyanate group: R—N=C=O) with difunctional amines (R—NH2) or alcohols (ROH), where R may be aliphatic, cycloaliphatic, aryl, hetero-aryl, or alkylaryl in nature. Such polyurethane structures are known to be strong, durable materials suitable for uses where they are in contact with biological solutions in living organisms, as described in U.S. Pat. No. 5,428,123.

The soft domains 2, 3, and 4 of the block copolymer confer permeability for both water solutions of compounds and for oxygen, but the dense non-porous nature of membranes cast from these polymers are adequate to exclude insoluble materials such as cells and suspensions of solid materials. Thus the membranes or fibers made from the multipolymers of the present invention allow aqueous solutes and oxygen to permeate the membranes while disallowing solid materials to pass through, as disclosed in U.S. Pat. No. 5,428,123.

In the present invention the resistance of the multipolymer and thus the resistance of membranes and fibers prepared from the multipolymer to biological degradation is increased by inclusion of domains of soft, biostable, relatively hydrophobic segments 4 consisting of polycarbonate-type materials (R—O—(CO)—O—R). Polycarbonates are oligomeric or polymeric materials where difunctional alcohols are linked via the difunctional carbonate group, where carbonate esters are formed linked to the difunctional alcohols through both available oxygen atoms of the carbonate moiety.

In the present invention, it has been discovered that multipolymers synthesized with specified proportions of the hard segment materials 1 and of the three distinct types of soft segment materials 2, 3, and 4 possess the desired properties of strength and durability, permeability to aqueous solutes and to oxygen, and chemical/physical stability while in contact with biological fluids in living organisms. The present invention comprises block copolymers or multi polymers wherein the hard segments 1 comprise 10–45 wt % of the total, and the soft segments 55–90 wt % of the total, where among the soft segments, the three necessary components comprise 5–25 wt % of total soft segment dry weight of oxygen-permeable materials 2, 5–25 wt % of total soft segment dry weight of hydrophilic materials 3, and 50–90 wt % of total soft segment dry weight of biostable, relatively hydrophobic materials 4, specifically polycarbonate-type materials.

The first preferred embodiment of the present invention for use in glucose sensors in contact with blood or interstitial fluids of the human body is characterized by the various types of suitable soft segment material types for the soft segment domains of the multipolymer. These include for the oxygen-permeable soft segments 2, oligomeric polysiloxane domains where the silicon-oxygen backbone may be substituted with various carbon-containing functional groups (—O—Si($R_2$)—)$_n$ where R is an alkyl, substituted alkyl, cycloalkyl, substituted cycloalkyl, aryl, or heteroaryl group and which oligomer is terminated with siloxy (Si—OH) moieties that may be combined via linkages such as ester, ether, or urethane with other segments of the polymer backbone; for the hydrophilic soft segments 3, poly-(oxyalkylene) chains such as poly-(oxyethylene) ($OCH_2CH_2$—)$_n$ or poly-(oxytetramethylene) ($OCH_2CH_2CH_2CH_2$—)$_n$ oligomeric or polymeric materials; for the biostable, relatively hydrophobic soft segments 4, polycarbonate chains where difunctional carbonate esters link difunctional alcohols such as ethylene, propylene, butylenes and higher glycols (—O($CH_2$)$_n$—O(CO)—)$_m$.

The specific properties of the polymers and of the membranes or fibers prepared from them can vary according to the specific nature and proportions of the various domains of the block copolymer, for instance if enhanced oxygen permeability is desired for a given use, the proportion of oxygen permeable polysiloxane soft segment 2 content can be increased; if increased biostability is desired, the proportion of biostable polycarbonate soft segment material 4 can be increased in the multipolymer. However in all cases the multipolymers of the present invention prepared according to these specifications possess properties of enhanced biostability relative to previously disclosed polymer compositions in applications where strength/durability, selective permeability of aqueous solutes and oxygen, and suitability for long-term exposure to biological fluids in living organisms are required.

In a second preferred embodiment of the present invention, the multipolymer may be used in sensors used for detecting the oxygen content of various biological fluids in the human body. In this embodiment of the invention, an oxygen-sensing electrode may be contained within a coating of the multipolymer, whose oxygen-permeable soft segment component 2 proportion has been adjusted to provide for a high degree of oxygen permeability enabling accurate detection of oxygen level, whose hydrophilic soft segment component 3 proportion has been adjusted to allow for free diffusion of the aqueous solutions of body fluids containing the dissolved oxygen through the multipolymer membrane, and whose biostable polycarbonate soft segment component 4 proportion has been adjusted to provide membrane stability in the presence of the reactive materials and enzymes contained within the body fluid in which the sensor is immersed.

These multipolymers can be prepared as outlined below in Example 1. More generally, the oligomeric polycarbonate soft segment domains may be included in the multipolymer through introduction of oligomeric polycarbonate materials into the reaction mixtures forming the multipolymer; the polycarbonate oligomers possess terminal reactive hydroxyl groups which can react with the isocyanate groups of the hard segment oligomers forming urethane linkages joining the ends of the polycarbonate soft segments to the ends of the polyurethane hard segments. The proportions of the polycarbonate soft segments in the multipolymer of the present invention may be controlled just as for the other soft segments of polysiloxanes and polyoxyalkylenes as described therein through control of the relative proportions of these components in the multipolymer-forming reaction.

The above described multipolymers may have sufficient permeability to oxygen and glucose, and adequate physical strength and durability for use in biological sensors of various types, and with resistance to biological degradation and oxidative breakdown in the human body.

Synthesis: General Considerations

An exemplary synthetic method is presented hereinbelow, based upon polyurethane chemistry, to teach how to make the polymers of this invention. Those skilled in the art will readily understand, however, based upon this disclosure, how to append surface-modifying endgroups (SMEs) to other segmented and block copolymers, random copolymers, graft copolymers, and homopolymers. The polymers of this invention may be prepared as solution-based polymers (dissolved in organic solvent), as thermoplastic polymers (100% solids, no solvent), as water-borne emulsions or dispersions (polymer dispersed in a water phase), or as two-component castable polymers. Synthetic procedures, which would enable the preparation of a multitude of polymers by changing soft segments, isocyanates, chain extenders, and/or endgroups, are described below. More details relating to the synthetic methods that may be employed to make the SME-containing polymers of this invention may be found in U.S. Pat. No. 5,589,563, the disclosure of which is hereby expressly incorporated by reference.

SYNTHETIC EXAMPLE 1

Solution-Based Synthesis

In this Example, the soft segments are polyhexyl ethyl carbonate diol (PHECD) having a molecular weight of 2000, polyethylene glycol (PEG)—having a molecular weight of 1500, and polydimethylsiloxane diol (PDMSD)—having a molecular weight of 1000, the hard segment is composed of 4,4'-diphenylmethane diisocyanate (MDI) having a molecular weight of 250.26 and ethylene diamine (ED) having a molecular weight of 60.1, and the endgroups are methoxy polyethylene glycol (mPEG) having a molecular weight of 2000 and mono-functional OH-terminated polydimethyl siloxane (mPDMS)—having a molecular eight of 2000. A reactor is charged with 8.6 moles of PHECD, 6.9 moles of PDMSD, 0.044 moles of mPDMS and 3.8 moles of PEG. The reactants are dried under vacuum with a nitrogen purge. Then 32.7 moles of 4,4'-diphenylmethane diisocyanate solution in dimethylacetamide is added to the reactor, and the contents of the reactor are further diluted with additional dimethylacetamide solvent. The ingredients are stirred for 3 hours at 55° C. The contents of the reactor are then diluted with more dimethylacetamide solvent, and cooled to 40° C. Polymer synthesis is completed by adding 12.5 moles of ethylene diamine in dimethylacetamide solvent and stirring at 40° C. for 30 minutes.

The resulting polymer has the following characteristics:

| Reactant | Molecular Weight | Weight-% | Moles |
|---|---|---|---|
| PHECD | 2000 | 41.8 | 8.6 |
| PEG | 1500 | 14.9 | 3.8 |
| PDMSD | 1000 | 18.8 | 6.9 |
| MDI | 250.26 | 22.3 | 32.7 |
| ED | 60.1 | 2.1 | 12.5 |
| mPDMS | 2000 | 0.24 | 0.044 |

The terms and expressions which have been employed in the foregoing specification are used as terms of description and not of limitation, and there is no intention, in the use of such terms and expressions, of excluding equivalents of the features shown and described or portions thereof, it being recognized that the scope of the invention is defined and limited only by the claims which follow.

The invention claimed is:

1. A biocompatible multipolymer, having a backbone comprising:
    (a) about 10 to 45 wt % of at least one hard segment;
    (b) about 55 to 90 wt % of soft segments, including:
        (i) 5 to 25 wt %, of total soft segment weight, of an oxygen permeable soft segment;
        (ii) 5 to 25 wt %, of total soft segment weight, of a hydrophilic soft segment;
        (iii) 50 to 90 wt %, of total soft segment weight, of a biostable, hydrophobic soft segment; and
    (c) having water absorption of from 2 to 25% of weight in membrane form.

2. The multipolymer of claim 1, wherein said biostable, hydrophobic soft segment is a polycarbonate.

3. The multipolymer of claim 1, wherein said hydrophilic soft segment has the chemical form $O(CH_2)_N$, where $N<4$.

4. The multipolymer of claim 3, wherein said hydrophilic soft segment is polyethylene oxide.

5. The multipolymer of claim 1, wherein said oxygen-permeable soft segment is polydimethylsiloxane.

6. The multipolymer of claim 1, further comprising capping end groups.

7. The multipolymer of claim 6, wherein said capping end groups comprise less than about 10 wt % of the total weight of said multi polymer.

8. The multipolymer of claim 1, capable of forming a membrane having a tensile strength of from 300 to 1,000 psi.

9. The multipolymer of claim 1, capable of forming a membrane having an ultimate elongation of 100 to 1,000%.

10. A glucose sensor, which senses glucose by way of oxidation and which includes a membrane that is permselective of oxygen and glucose, said membrane comprising:
    a biocompatible multipolymer having water absorption of from 2 to 25% of dry weight in membrane form, and having a backbone comprising about 55 to 90 wt % of soft segments including:
        (i) 5 to 25 wt %, of total soft segment weight, of an oxygen permeable soft segment;
        (ii) 5 to 25 wt %, of total soft segment weight, of a hydrophilic soft segment; and
        (iii) 50 to 90 wt %, of total soft segment weight, of a biostable, hydrophilic soft segment.

* * * * *